(12) United States Patent
Odon

(10) Patent No.: US 9,247,958 B2
(45) Date of Patent: Feb. 2, 2016

(54) DEVICE FOR EXTRACTING ELEMENTS FROM A CAVITY

(75) Inventor: Jorge Ernesto Odon, Banfield (AR)

(73) Assignee: AIR BAG ONE SARL, Luxembourg (LU)

( * ) Notice: Subject to any disclaimer, the term of this patent is extended or adjusted under 35 U.S.C. 154(b) by 545 days.

(21) Appl. No.: 12/669,754

(22) PCT Filed: Jul. 18, 2008

(86) PCT No.: PCT/ES2008/070143
§ 371 (c)(1),
(2), (4) Date: May 26, 2010

(87) PCT Pub. No.: WO2009/013383
PCT Pub. Date: Jan. 29, 2009

(65) Prior Publication Data
US 2010/0241134 A1    Sep. 23, 2010

(30) Foreign Application Priority Data
Jul. 20, 2007   (AR) ............................... 20070103245

(51) Int. Cl.
*A61B 17/42*    (2006.01)
*A61B 17/44*    (2006.01)
(Continued)

(52) U.S. Cl.
CPC ............... *A61B 17/42* (2013.01); *A61B 17/442* (2013.01); *A61B 17/50* (2013.01); *A61F 11/006* (2013.01)

(58) Field of Classification Search
CPC .... A61B 17/42; A61B 17/4241; A61B 17/44; A61B 17/46; A61B 17/48

USPC ......... 606/110–113, 115, 119, 121–123, 127; 600/562, 565, 37
See application file for complete search history.

(56) References Cited

U.S. PATENT DOCUMENTS

| 1,162,516 A | 11/1915 | Davis |
| 1,782,814 A | 11/1930 | Froehlich |

(Continued)

FOREIGN PATENT DOCUMENTS

| AR | 060105329 A1 | 2/2008 |
| CN | 1524499 A | 9/2004 |

(Continued)

OTHER PUBLICATIONS

"Bag Definition"—Merriam-Webster Dictionary, accessed Jun. 9, 2014.*

(Continued)

*Primary Examiner* — Ryan Severson
*Assistant Examiner* — Rachel S Papeika
(74) *Attorney, Agent, or Firm* — Sughrue Mion, PLLC

(57) ABSTRACT

A device to extract elements contained in a cavity, additional to patent of invention P060105329, and of preferable application to assistance at childbirth and/or extraction of elements seated in cavities of the human body, facilitating the task of medical professionals. Said device is comprised of a bag having one of its ends open, through which it is possible to introduce the element to be extracted, in which, in a first embodiment and on the outer surface of the bag and along all its circumference line, there is at least one air chamber being able to get in contact with the element to be extracted when receiving inner pressure, being said chamber connected to a pressure generating means; and in a second embodiment, an outward fold is defined on said bag, forming an annular cavity at the time it gets in contact with the cavity containing the element to be extracted.

25 Claims, 4 Drawing Sheets

(51) Int. Cl.
*A61B 17/50* (2006.01)
*A61F 11/00* (2006.01)

(56) References Cited

U.S. PATENT DOCUMENTS

| | | | | |
|---|---|---|---|---|
| 2,637,320 | A * | 5/1953 | Greenberg | 606/122 |
| 4,243,040 | A * | 1/1981 | Beecher | 606/127 |
| 4,469,100 | A * | 9/1984 | Hardwick | 606/127 |
| 4,875,482 | A * | 10/1989 | Hariri et al. | 606/122 |
| 5,312,385 | A * | 5/1994 | Greco | 604/356 |
| 5,593,413 | A | 1/1997 | Alexander | |
| 5,910,146 | A | 6/1999 | Alexander | |
| 6,270,505 | B1 * | 8/2001 | Yoshida et al. | 606/127 |
| 6,695,791 | B2 * | 2/2004 | Gonzalez | 600/562 |
| 6,846,029 | B1 | 1/2005 | Ragner et al. | |
| 2002/0013601 | A1 | 1/2002 | Nobles et al. | |
| 2004/0015175 | A1 | 1/2004 | Nguyen | |

FOREIGN PATENT DOCUMENTS

| | | |
|---|---|---|
| DE | 19747822 A1 | 7/1999 |
| FR | 2450113 A2 | 9/1980 |
| GB | 1162516 A | 8/1969 |
| JP | 6-217991 A | 8/1994 |
| WO | 97/02785 A1 | 1/1997 |
| WO | 98/03123 A1 | 1/1998 |
| WO | 03/002822 A1 | 1/2003 |
| WO | 2005/025427 A1 | 3/2005 |
| WO | 2008/068367 A1 | 6/2008 |

OTHER PUBLICATIONS

Supplementary European Search Report issued Jul. 29, 2011 in a corresponding European Patent Application No. 08805389.7.
Official Action issued Jan. 30, 2012 in Eurasian Patent Application No. 201070178.
Hessburg et al., "An Assisted Obstetric Delivery Device for Resource-limited Settings," Intl. J. for Service Learning in Engineering 7:1-12, Fall 2012.
Patent Examination Report No. 1 issued in Australian Patent Application No. 2008278919 dated Nov. 20, 2012.
Notice of Reasons for Rejection issued in Japanese Patent Application No. 2010-517426 dated Oct. 9, 2012.
Chinese Office Action issued in Chinese Patent Application No. 200880025355.9.

* cited by examiner

DEVICE FOR EXTRACTING ELEMENTS FROM A CAVITY

The present invention relates to a device to extract elements contained in a cavity; said device allows to perform the method of extraction described and claimed in patent application No. P060105329 submitted in Argentina on Dec. 1, 2006 and not published up to the date this application is filed.

The proposed device is preferably used to assist at childbirth and/or to extract elements seated in cavities of the human body, facilitating the task of medical professionals.

Along with the uncountable uses of the present invention and that of the method of said patent application No. P060105329, we find this invention applicable in the field of gastroenterology, in cases such as: extraction of rectal foreign bodies, extraction of esophagogastric foreign bodies and extraction of biliary stones; in the field of urology: in cases such as extraction of urinary tract stones, extraction of elements accidentally displaced along with medical instrumental; in the field of vascular surgery: in cases such as clot displacement and/or vascular prosthesis or to revascularize critical organs, and, lastly in the field of otorrinolaringology: in cases such as extraction of foreign bodies impacted in ears or nostrils and for cerumen extraction.

PRIOR ART OF THE INVENTION AND ITS IMPROVEMENTS

In relation to the prior art of this invention and, in particular, in the field of neonatology, reference may be made to the tools and accessories presently used at childbirths, among which the most popular are those called "forceps", which use has caused irreparable harm in newborns.

The device disclosed by application P060105329 is known to us as able to perform the proposed method and it comprised one, two or more flexible bags or containers, each of them with a handle, that had to be inserted by the medical professional for the extraction, for instance, of a baby.

In examinations conducted with equivalent materials and elements, it was noted that the use of said devices at childbirth gave rise to problems in the insertion of the bags into the uterine cavity, in particular, while trying to surround the fetus. As well, there was a possibility that the health professional may make an incorrect movement during extraction causing injuries to the vagina of the woman in labor.

Those problems were deeply examined and have been solved with the present device, which comprises a bag or flexible container open on one of its ends, and on which outer surface a closed air-containing element or chamber is fixed or defined, the latter being connected to an air injection means, having a traction handle that closes the other end of the bag at the time of its assembly.

It is important to emphasize that for any of the devices used to perform the extraction method stated in patent application No. P060105329, the responsibility for the timely decision to use the device will lie on the health professional, who will assess the specific conditions of every birth or the techniques to be used.

It is expected that the utilization of this device will do away with or reduce the use of forceps or other vacuum generating devices, which pose great risk when used in assistance to delivery.

MAIN OBJECT OF THE PRESENT INVENTION

The device of the present invention is initially comprised of a bag with its two ends open, one of them is closed at the traction handle, on which outer surface an air chamber is positioned, and then an outward fold is made on the open bag. Said closed chamber is connected to a cannula or pipe that crosses the bag until reaching the screw-shaped piece that is part of the traction handle of the present extraction device. A disk-shaped piece will allow apart from the fastening of the bag on to the traction handle, that the bag keeps its round section with the same diameter throughout the device, which will facilitate the extraction of the baby's head while coming out of the vagina. A cannula or pipe to feed air to the chamber will run inside the handle previously crossing the conical body, coming out by the handle's end until reaching a presostatic measuring or indicating gauge and an air pump. Said pump will feed air to the chamber up to a desired pressure; it will be possible to release air in case pressure is exceeding or when endangers the outcome of the extraction method. The preferred fastening of the bag will be made between the disk and a conical body, the mentioned screw-shaped piece will tighten one against the other and will screw its threaded end into a pertinent hole made in the inner of the handle.

Said open bag and chamber shall be preferably made of extremely flexible material, film-type of some microns wide, with a highest traction resistance, said material being hypoallergenic and covered with fine lubricating jel.

Said open bag with its external air chamber around itself shall be inserted by the medical professional between the head of the fetus and the uterine cervix, after breaking waters has taken place. To accomplish this, he could use an outward fold to be made on the bag, pushing with a flat spatula-type instrument from inside the line of the fold until placing said bag on the fetus' shoulders. Sometimes, the professional could resort to the ecographic images, by means of which he will see that the mentioned bag reaches the desired position. Said fold shall approximately and preferably be made at the furthest level of the air chamber.

Once the bag is placed at the level of the fetus' shoulders, the chamber will be filled with air by means of a cannula or pipe, which enters the interior of the bag and the traction handle of the device of the present invention, crossing said bag until reaching the mentioned air chamber. Once the chamber is filled with air at the necessary pressure, the only thing to do is to pull on the traction handle of the device so as to extract the baby, and thus a simple delivery is achieved with no traumatism at all.

The end of the bag, opposed to that of the handle, shall be inserted through the cervix of the uterus.

In a preferable embodiment, the air chamber shall comprise of a regulating and compensating valve for the inlet of air or another fluid of very low pressure, which valve shall be calibrated to act as an air outlet valve pursuant to the adjustment selected by the tocogynelogist professional. As part of this system, it shall be possible to use, in an external manner, a presostatic measuring or indicating gauge that will be of help for the assisting professional.

It is important to maintain a controlled inner pressure in the air chamber since the value of said pressure may increase when extracting the flexible element from the interior of the cavity up to values that may complicate the extraction due to the increase of volume that causes this greater generated pressure. Said regulating valve shall be a relief valve for this generated pressure, avoiding that said pressure raises beyond a predetermined value.

BRIEF DESCRIPTION OF THE FIGURES

In order to better understand the object of this present invention, some schematic figures shall illustrate the invention, in its preferred embodiment, which are included by way of example, in which.

In said figures, equal references correspond to identical elements of the invention.

DETAILED DESCRIPTION OF THE INVENTION

Figure 1:
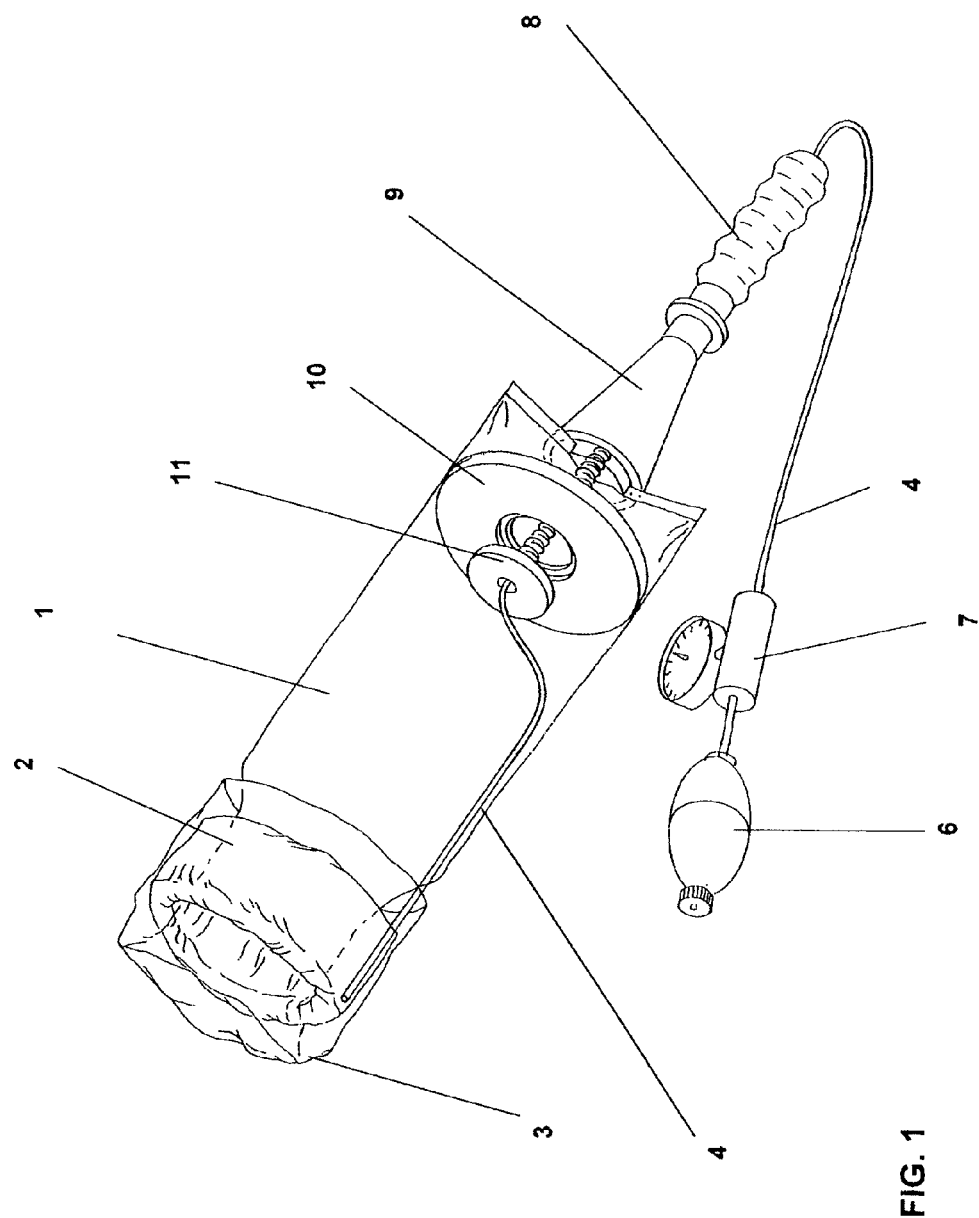
FIG. 1 illustrates a perspective view of the device for the extraction of elements of the present invention in a first preferred embodiment.

In FIG. 1, it is seen that the device in the first preferred embodiment is comprised of a bag 1 with one of its ends (1a) open, on which outer surface an air chamber is positioned or defined, and then an outward fold 3 is made on the open bag 1. Said closed chamber 2 is connected to a cannula or pipe 4 that crosses the bag 1 until reaching a screw-shaped piece 11 with a pushing disk that is part of the traction handle 5 of the present extraction device. In this figure, piece 11 is seen, as well as the fitting ring 10, in an open position in order to facilitate the understanding of how the closed end 1b of the bag 1 is fixed to the traction handle.

Said fitting ring 10 (of variable shape and diameter, according to the characteristics of the delivery) allows not only the fastening of the bag to the traction handle 8 but also that said bag maintains a determined round section, which will facilitate the extraction of the fetus' head at the time it exits the vagina. The mentioned disk may vary in diameter and also may be removed from the device.

The cannula or pipe 4 for feeding air into the chamber 2 shall enter the interior of the handle previously passing the conical body 9, coming out by the end of the handle until reaching a preostatic measuring and indicating gauge 7 and an air pump 6. From said pump 6, air will be supplied into the chamber until a desired pressure; it shall be possible to release air in case pressure is exceeding or when it endangers the successful outcome of the extraction method.

The preferred fastening of the bag 1 shall be made between the fitting ring 10 and the conical body 9, the screw of the screw-shaped piece 11 shall tighten one against the other and shall screw its threaded end into a pertinent hole made in the interior of the handle 8.

Figure 2:
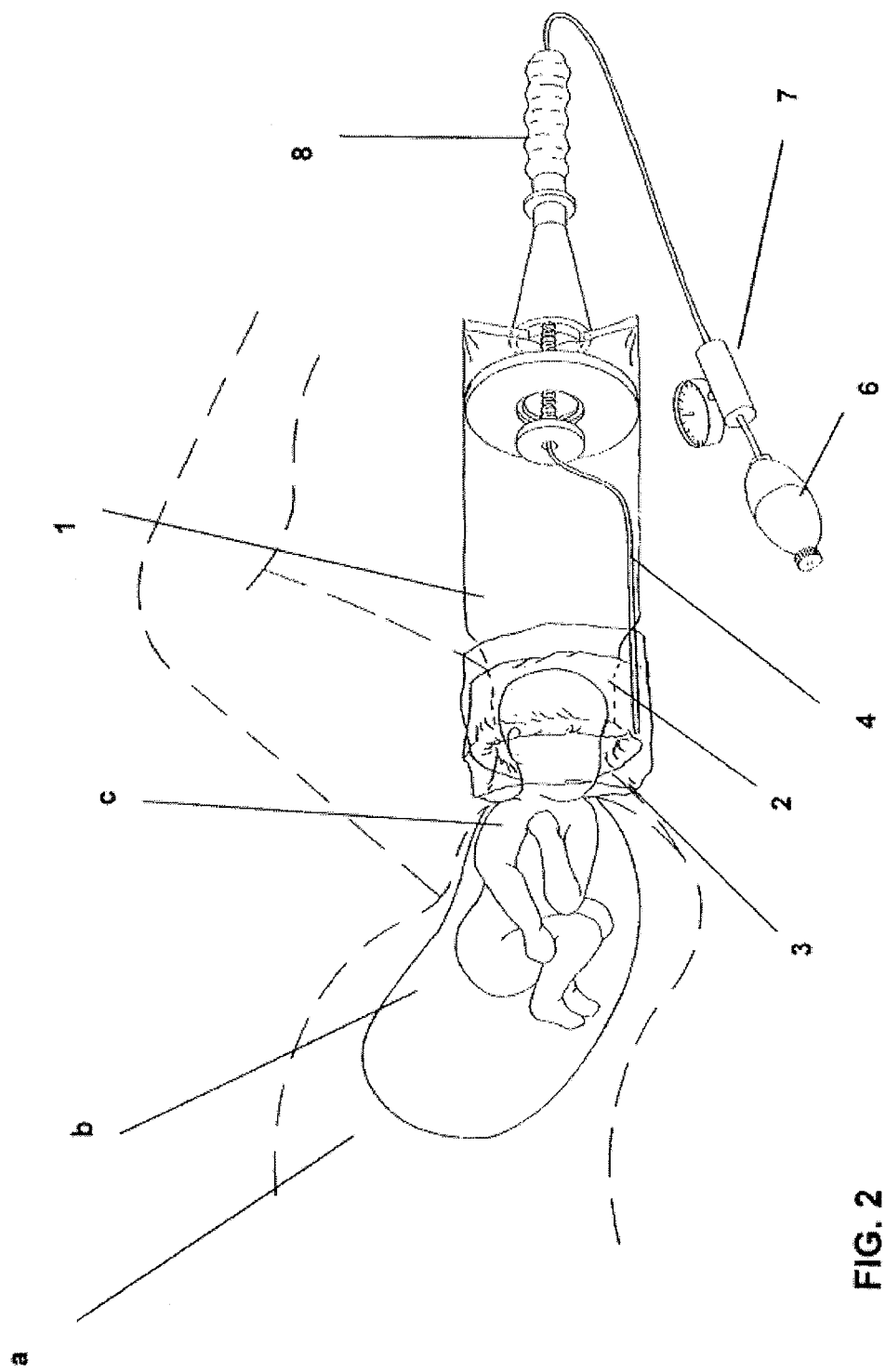
FIG. 2 allows to see the application of the device of the first embodiment of this invention in the extraction of a baby, preferably.

FIG. 2 shows a schematic view of the fitting of the device of FIG. 1 in a preferred use of same at a stage of the delivery. Here it is possible to see a woman "a" in whose womb "b" there is her fetus "c"; the bag 1, that is part of the device of the present invention, is fitted taking advantage of the fold 3 of the bag 1, either with the hand or with a thin element that slides between the bag and the external fold, allowing to move the chamber 2 to a position close to the neck of fetus "c".

Once the device of the present invention is placed, the chamber 2 shall be filled with air, operating the air pump 6 and controlling the pressure by means of the presostatic measuring and indicating gauge 7. Once said chamber is filled, the only thing to be made is to gently pull, in a straight direction, by the traction handle 8, accompanying the woman's pushes and also accompanying the gentle exit of air that was insufflated into the device; hence the extraction of the fetal cephalic pole is obtained.

The greatest volume attained in the external air chamber when extracting the fetus is due to the fact that at the time of the extraction, the fluid contained therein is retained in the section that lies in the interior of the cavity, and therefore, said greater pressure shall better fix the fetus that shall be moved within the bag as if on a conveyor belt.

Said annular chamber having a shape of an inflated ring shall adopt, due to its manufacturing design, a conical shape that allows to properly position the fetus' head.

In summary and to clearly understand the way to use the device described in the preceding paragraphs, the steps to be performed are mentioned as follows:

Insertion of bag 1 into the uterus until the air chamber makes contact with the fetus' shoulders.

At this stage, the woman in labor shall be in a normal delivery position.

Entrance of air or another fluid at very low pressure into the air chamber 3 by means of the air pump 6.

At this stage, the assisting professional shall proceed to insufflate air through the valves until noting, aided by an ecographer, if necessary, the distribution of the air chamber among the spaces and intertices of the fetal head and the mother's uterus. The reading of the presostatic measuring gauges shall assure the control of internal pressures, which shall never be higher than those pressures generated in the uterine wall.

Traction exerted by the obstetrician accompanied by the pushes of labor.

The physician shall proceed to collaborate with the woman in labor, accompanying the contractions and pushes with the synchronized traction of the handle that holds the closed end of the bag. The fetus shall slip within the bag as moved by a conveyor belt. Valves which at first were used for the entrance of insufflated air, shall now work to compensate pressure; it will be possible to expel part of the air and maintain the necessary pressure to assist the "virtual push" caused by the traction made by the professional from the chambers or probes.

Figure 3:
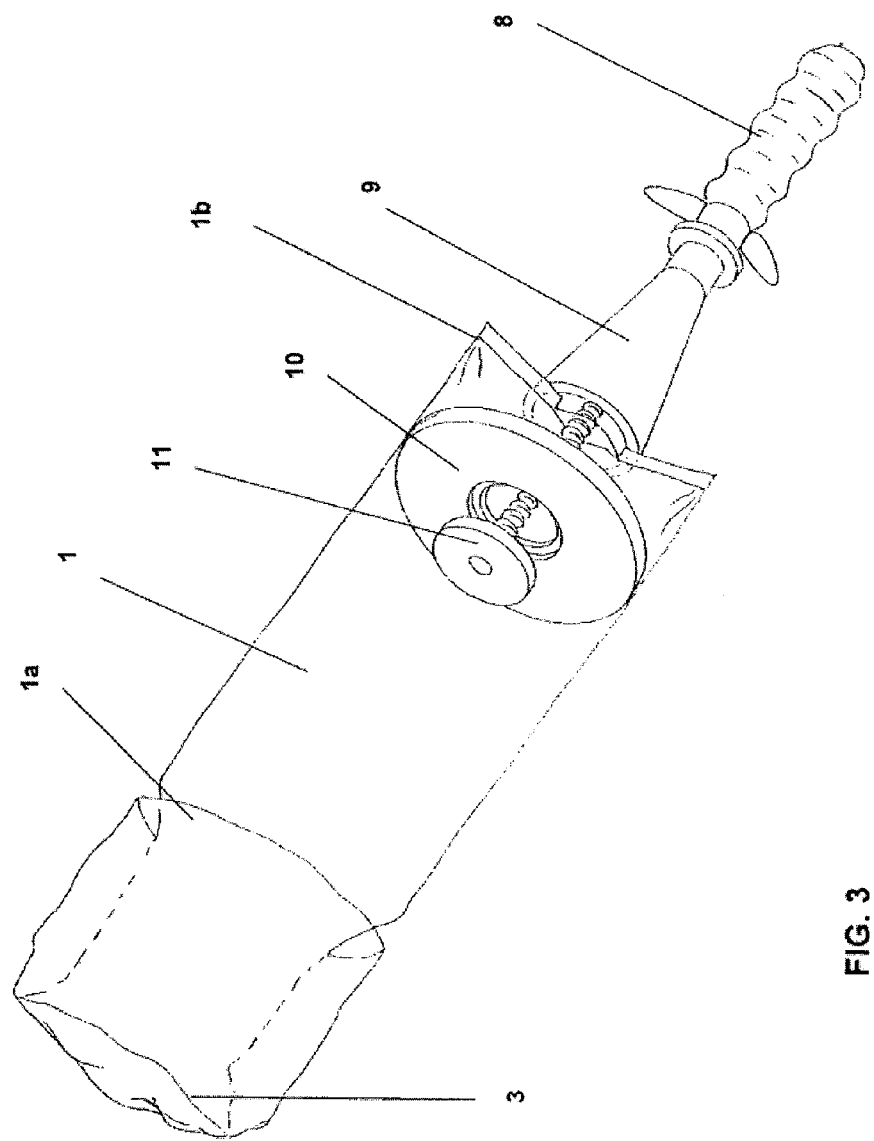
FIG. 3 shows a perspective view of the device for the extraction of elements of the present invention in a second preferred embodiment.
Figure 4:
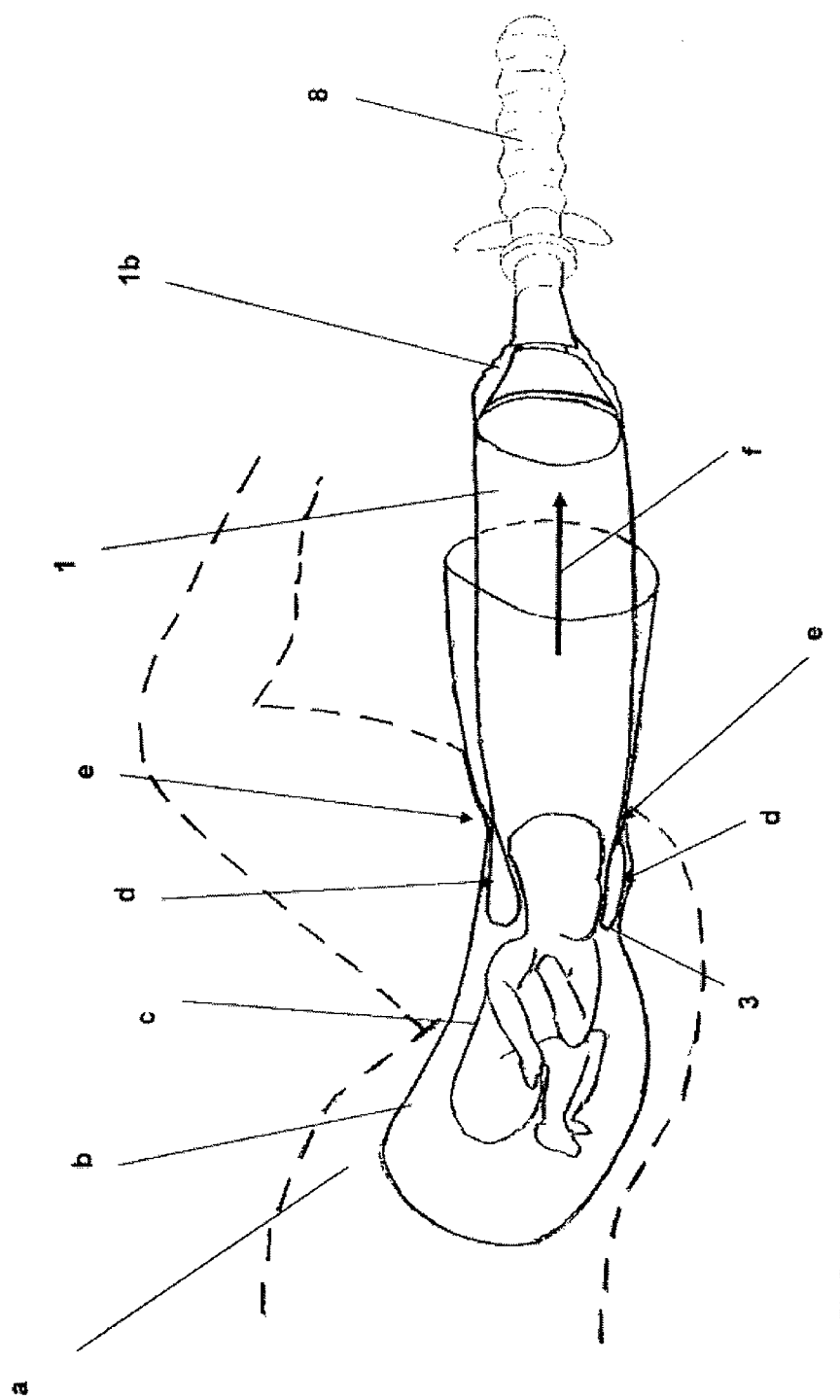
FIG. 4 allows to see the application of the device of the second embodiment of this invention in the extraction of a baby, preferably.

In the second preferred embodiment of the device, as shown in FIGS. 3 and 4, the round air chamber of the first embodiment is no longer incorporated. Said air chamber shall be formed in the round inner cavity "d" of fold 3 of bag 1, at the time the outer surface of the bag's end makes contact with the outer surface of the same bag 1. This nearness of surfaces shall be forced when passing through the uterus cervix and by the inner walls of the vagina. The air accumulated in said round cavity "d" shall act as part of a clamp that moves in all directions (a 360° revolving clamp).

FIG. 4 shows the "conveyor belt" phenomenon.

Bag 1, in any of the preferred embodiments of this invention, has, at the area where it will contact "e" the cavity walls (or vagina walls in case of childbirth), a sufficient and necessary rugosity so as to provide a fixed fastening surface. The inner face of bag 1 is designed without rugosity: it is smooth and treated with liquid or gel to support the slipping function of the virtual "conveyor belt".

When pulling from the traction handle 8, the rugose surface "d" shall get adhered or attached to the face contacting the tunnel or cavity that contains the element, the round cavity "d" shall act as an "air fastening clamp", able to move in all directions, and shall displace the object to be extracted as if on a "conveyor belt" between the inner faces of the bag 1 (movement of arrows "f").

This so-called "conveyor belt", which in its inner part holds the object to be extracted, protects against friction in the outlet channel and facilitates the extraction of the object since the rubbing of the conveyor belt takes place between the walls of the device.

The "air fastening clamp" is made with the natural air chamber (round inner cavity "d" formed adjacently to the fold) which is created during the placement of the device. As well, this "air fastening clamp" facilitates the dilation of the outlet channel.

Alternatively and pursuant to the professional's option, one of the two preferred embodiments may be used, that is: with external air chamber 2, chamber 2 that will be connected to an external pressure generating means; without external air chamber 2 and with an external pressure generating means; and finally, without any external air chamber 2 and without any external pressure generating means.

The device of the present invention in its two preferred embodiments shall allow to accompany the birth of the fetus, holding same with a round air chamber, with no risk at all for the child or the mother. In particular, it shall be of great help for the woman in labor so that, during a long expulsion stage, the obstetrician may provide assistance during the extraction of the fetus without using any rigid mechanical tools that may harm any of the parties.

On a separate note and with the corresponding technological sufficiency, this novel system can find other applications in many fields of the industry, to with pipes of big diameter such as gas pipes, oil ducts or poly ducts, or of medium or small diameter, such as water, gas, telephone and power supply nets.

It is undoubtly understood that when the present invention is put into practice, changes to certain manufacturing details and shape, may be made, without departing from the main principles which are clearly stated in the following claims.

The invention claimed is:

1. A device to extract an element contained in a cavity comprising:
    a bag comprising an opening for receiving the element;
    an outer layer comprising an open end facing an opposite direction to the opening of the bag, wherein the outer layer is positioned at or near the open end of the bag such that the outer layer overlaps and extends along a portion of a surface of the bag and wherein the outer layer is configured to slide relative to the portion of the surface of the bag that the outer layer overlaps; and
    at least one inflatable chamber distinct from the outer layer and positioned at or near the open end of the bag wherein the volume of the chamber is variable so as to reduce an inner circumference of the bag when the chamber is inflated and wherein the chamber has an outer surface facing radially outward and at least a portion of the outer layer extends over the outer surface of the chamber, and wherein the outer layer is configured to slide relative to the outer surface of the chamber.

2. The device according to claim 1, wherein the outer layer is a folded portion of the bag.

3. The device according to claim 1, wherein the chamber surrounds a portion or an entire circumference of the bag.

4. The device according to claim 1, wherein the chamber is formed as an inseparable part of the bag.

5. The device according to claim 1, wherein the chamber when inflated has a conical shape or an annular shape.

6. The device according to claim 1, further comprising control means for at least one of controllably inflating or deflating the chamber.

7. The device according to claim 6, wherein the control means comprises at least a pipe connected at one end of the pipe to the chamber and at another end of the pipe to a pump.

8. The device according to claim 1, further comprising a traction handle attached to at least one end of the bag.

9. The device according to claim 8, wherein the traction handle comprises:
    a fitting ring;
    a hollow handle configured to receive a screw shaped piece;
    the screw shaped piece that holds the fitting ring to the hollow handle and to at least one end of the bag.

10. The device according to claim 9, wherein the fitting ring has a diameter according to the opening of the cavity.

11. The device according to claim 1, wherein the cavity is a uterine channel and the device is configured to extract an element in the uterine channel.

12. The device according to claim 1, wherein a surface of the outer layer is configured to contact the cavity and has higher rugosity than the portion of the surface of the bag overlapped by the outer layer.

13. The device according to claim 1, wherein a lubricating gel is between the outer layer and the portion of the bag that the outer layer overlaps.

14. The device according to claim 1, wherein the chamber is located only where the outer layer overlaps and extends along at least a portion of the bag so that outer layer extends over the chamber before inserting the device in the cavity.

15. The device according to claim 1, wherein the open end of the outer layer allows access to an area where the outer layer overlaps and extends along a portion of the surface of the bag.

16. A method for extracting an element contained in a cavity comprising:
    providing the device of claim 1;
    identifying an element to be extracted wherein the element in contained in a cavity;
    fitting the open end of the bag and the outer sheath around at least a portion of the element;
    permitting the element to slip inside the bag;
    grasping the element using the means for grasping the element; and
    extracting the element outside the cavity by allowing the overlapping surface between the bag and the sheath to slip.

17. The method according to claim 16, wherein bag and the outer sheath are extended around the element such that the overlapping surface between the bag and the outer sheath forms a seal due to the element pressing against an inner wall of the cavity through the bag so as to define a sealed chamber such that upon inflation the sealed chamber forms the means for grasping the element.

18. The method according to claim 17, further comprising inflating the sealed chamber to grasp the element.

19. A device to extract an element contained in a cavity, comprising:
    a bag comprising at least opening for receiving the element;
    at least one inflatable chamber positioned at or near the open end of the bag wherein the inflatable chamber includes one or more outer walls defining an inflatable volume such that the chamber decreases an inner circumference of the bag upon inflation wherein the inflatable chamber extends along a portion or an entire circumference of the bag; and
    an outer layer comprising at least one open end facing in an opposite direction to the opening of the bag, wherein the outer layer is positioned radially outward of the chamber and at or near the opening of the bag wherein the outer layer is configured to abut the cavity, overlaps and extends along at least a portion of the inflatable chamber, and is in sliding abutment with at least a portion of the one or more outer wall of the chamber.

20. The device according to claim 19, wherein the outer layer is a folded portion of the bag.

21. The device according to claim 19, wherein the chamber when inflated has a conical shape or an annular shape.

22. The device according to claim 19, wherein the chamber is located where the outer layer overlaps and extends along at least a portion of the bag so that outer layer extends over the chamber before inserting the device in the cavity.

23. The device according to claim 19, wherein the open end of the outer sheath allows access to an area where the outer sheath overlaps and extends along a portion of the surface of the bag.

24. A device to extract an element contained in a cavity wherein said device comprises:

a bag having at least one open end, an outward fold formed at said open end and extended back along a portion of the bag such that the outward fold has at least one open end distinct from the open end of the bag wherein the open end of the outward fold allows access to an area where an inner surface of the fold overlaps and extends along a portion of a radial outer surface of the bag, and at least one annular chamber formed in the bag, only in said portion of the bag where the fold is extended, wherein said annular chamber is an air chamber formed in the bag positioned between the radial outer surface of the bag and the inner surface of the fold, and surrounding the bag along the entire circumference of the bag, wherein said annular chamber is capable of grasping the element to be extracted when inflated.

25. The device according to claim 24, wherein the open end of the outward fold faces in a direction opposite to the open end of the bag.

* * * * *